United States Patent
Magatani et al.

(10) Patent No.: US 9,162,954 B2
(45) Date of Patent: Oct. 20, 2015

(54) CATALYST AND PROCESS FOR PREPARING ACROLEIN AND/OR ACRYLIC ACID BY DEHYDRATION REACTION OF GLYCERIN

(71) Applicant: ARKEMA FRANCE, Colombes (FR)

(72) Inventors: Yasuhiro Magatani, SanyoOnoda (JP);
Kimito Okumura, SanyoOnoda (JP);
Jean-Luc Dubois, Millery (FR);
Jean-Francois Devaux, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/491,433

(22) Filed: Sep. 19, 2014

(65) Prior Publication Data
US 2015/0005526 A1    Jan. 1, 2015

Related U.S. Application Data

(62) Division of application No. 13/496,339, filed as application No. PCT/JP2009/067115 on Sep. 18, 2009, now abandoned.

(51) Int. Cl.

| | |
|---|---|
| C07C 45/00 | (2006.01) |
| C07C 51/00 | (2006.01) |
| C07C 253/00 | (2006.01) |
| B01J 27/182 | (2006.01) |
| B01J 27/186 | (2006.01) |
| B01J 27/19 | (2006.01) |
| B01J 27/198 | (2006.01) |
| B01J 27/199 | (2006.01) |
| B01J 23/00 | (2006.01) |
| B01J 23/30 | (2006.01) |
| B01J 27/188 | (2006.01) |
| B01J 37/02 | (2006.01) |
| C07C 45/52 | (2006.01) |
| C07C 51/25 | (2006.01) |
| C07K 14/78 | (2006.01) |
| G01N 33/68 | (2006.01) |
| B01J 21/06 | (2006.01) |
| B01J 21/12 | (2006.01) |
| C07C 51/235 | (2006.01) |
| C07C 253/26 | (2006.01) |

(52) U.S. Cl.
CPC ............ *C07C 45/002* (2013.01); *B01J 21/063* (2013.01); *B01J 21/12* (2013.01); *B01J 23/002* (2013.01); *B01J 23/30* (2013.01); *B01J 27/188* (2013.01); *B01J 37/0205* (2013.01); *C07C 45/52* (2013.01); *C07C 51/235* (2013.01); *C07C 51/252* (2013.01); *C07C 253/26* (2013.01); *C07K 14/78* (2013.01); *G01N 33/6887* (2013.01); *G01N 33/6893* (2013.01); *B01J 2523/00* (2013.01); *G01N 2333/705* (2013.01)

(58) Field of Classification Search
CPC ........ B01J 27/182; B01J 27/186; B01J 27/19; B01J 27/198; B01J 27/199; C07C 45/00; C07C 51/00; C07C 51/235; C07C 253/00
USPC ........... 558/315; 568/485, 486, 471; 562/532, 562/599; 502/208–212, 214
IPC ................ B01J 27/182,27/186, 27/19, 27/198, B01J 27/199; C07C 45/00, 51/00, 51/235, C07C 253/00
See application file for complete search history.

(56) References Cited

U.S. PATENT DOCUMENTS

| | | |
|---|---|---|
| 3,379,651 A | 4/1968 | Hargis et al. |
| 4,870,217 A | 9/1989 | Knifton et al. |
| 4,876,397 A | 10/1989 | Knifton et al. |
| 4,898,987 A | 2/1990 | Knifton et al. |
| 4,898,995 A | 2/1990 | Knifton et al. |
| 4,983,565 A | 1/1991 | Knifton et al. |
| 5,297,450 A | 3/1994 | MacPherson |
| 5,300,703 A | 4/1994 | Knifton |

(Continued)

FOREIGN PATENT DOCUMENTS

| | | |
|---|---|---|
| CN | 1583253 A | 2/2005 |
| CN | 1792446 A | 6/2006 |

(Continued)

OTHER PUBLICATIONS

International Search Report issued on Oct. 29, 2010 in the corresponding PCT/JP2009/067115.
Office Action for related Chinese Patent Application No. 201210213673.X dated Jan. 28, 2014.
English Translation of Office Action for related Chinese patent Application No. 201210213673.X dated Jan. 28, 2014.
Extended Search Report for Related European Patent Application No. 13191431.9 dated Apr. 2, 2014.
Office Action for Related Japanese Patent Application No. 2012-529412 dated Mar. 25, 2014.
English Translation of Office Action for Related Japanese Patent Application No. 2012-529412 dated Mar. 25, 2014.
Office Action for Related Japanese Patent Application No. 2012-202968 dated Apr. 22, 2014.

(Continued)

*Primary Examiner* — Patricia L Hailey
(74) *Attorney, Agent, or Firm* — Millen, White, Zelano & Branigan, P.C.

(57) ABSTRACT

A catalyst composition comprising at least an heteropolyacid deposited on a porous titania carrier.
A catalyst composition comprising at least an heteropolyacid in which protons in the heteropolyacid may be partially exchanged by at least one cation selected from elements belonging to Group 1 to Group 16 of the Periodic Table of Elements that have been deposited on a porous titania carrier.
A method for preparing the catalyst composition, comprising impregnating a titania carrier with a solution of at least one metal selected from elements belonging to the Group 1 to Group 16 of the Periodic Table of Elements or onium, drying and firing the resulting solid mixture, secondly impregnating the resulting solid mixture with a solution of heteropolyacid, drying, and firing the resulting solid mixture.
A process for preparing acrolein and acrylic acid by dehydration of glycerin, carried out in the presence of the catalyst.

26 Claims, No Drawings

(56) References Cited

U.S. PATENT DOCUMENTS

| | | | |
|---|---|---|---|
| 5,510,308 | A | 4/1996 | Kourtakis |
| 5,710,225 | A | 1/1998 | Johnson et al. |
| 5,866,739 | A | 2/1999 | Soled et al. |
| 5,919,725 | A | 7/1999 | Soled et al. |
| 6,313,343 | B1 | 11/2001 | Arita et al. |
| 6,376,706 | B2 | 4/2002 | Kitchen et al. |
| 6,472,556 | B2 | 10/2002 | Kitchen et al. |
| 7,396,962 | B1 | 7/2008 | Dubois et al. |
| 7,531,699 | B2 | 5/2009 | Dubois et al. |
| 7,625,651 | B2 | 12/2009 | Kim et al. |
| 7,655,818 | B2 | 2/2010 | Dubois et al. |
| 7,880,034 | B2 | 2/2011 | Dubois et al. |
| 7,910,771 | B2 | 3/2011 | Dubois et al. |
| 8,212,070 | B2 | 7/2012 | Dubois et al. |
| 8,252,960 | B2 | 8/2012 | Dubois et al. |
| 2001/0012818 | A1 | 8/2001 | Kitchen et al. |
| 2001/0049335 | A1 | 12/2001 | Kitchen et al. |
| 2003/0099874 | A1 | 5/2003 | Kim et al. |
| 2008/0146852 | A1 | 6/2008 | Dubois et al. |
| 2008/0183013 | A1 | 7/2008 | Dubois et al. |
| 2008/0214880 | A1 | 9/2008 | Dubois et al. |
| 2008/0319233 | A1 | 12/2008 | Dubois et al. |
| 2009/0018362 | A1 | 1/2009 | Dubois et al. |
| 2010/0048850 | A1 | 2/2010 | Dubois et al. |
| 2010/0068595 | A1 | 3/2010 | Kim et al. |
| 2010/0168471 | A1 | 7/2010 | Dubois et al. |
| 2011/0112330 | A1 | 5/2011 | Magatani et al. |
| 2011/0160491 | A1 | 6/2011 | Dubois et al. |
| 2013/0066100 | A1* | 3/2013 | Magatani et al. ............. 558/315 |

FOREIGN PATENT DOCUMENTS

| | | |
|---|---|---|
| CN | 101119955 A | 2/2008 |
| EP | 0 367 408 A2 | 5/1990 |
| EP | 0 375 257 A2 | 6/1990 |
| EP | 0375257 A2 | 6/1990 |
| EP | 0967009 A2 | 12/1999 |
| EP | 1 309 025 A2 | 5/2003 |
| GB | 1 025 679 A | 4/1966 |
| JP | 4-139149 A | 5/1992 |
| JP | 2001-232207 A | 8/2001 |
| JP | 2008-88149 A | 4/2008 |
| JP | 2010-511039 | 4/2009 |
| WO | 2006 087083 | 8/2006 |
| WO | 2006 114506 | 11/2006 |
| WO | 2007 058221 | 5/2007 |
| WO | 2007 090990 | 8/2007 |
| WO | 2007 090991 | 8/2007 |
| WO | 2008 087315 | 7/2008 |
| WO | 2008 113927 | 9/2008 |
| WO | 2009/127889 A1 | 10/2009 |
| WO | 2009 128555 | 10/2009 |
| WO | 2009 136537 | 11/2009 |

OTHER PUBLICATIONS

English Translation of Office Action for Related Japanese Patent Application No. 2012-202968 dated Apr. 22, 2014.
Communication from the EPO dated Dec. 3, 2013, regarding the partial European Search Report for related Patent Application No. 13191431.9.
Office Action for related Korean Patent Application No. 2012-7008519 dated Aug. 23, 2013.
English Translation of Office Action for related Korean Patent Application No. 2012-7008519 dated Aug. 23, 2013.
Office Action for related Korean Patent Application No. 2013-7027958 dated Jan. 10, 2014.
English Translation of Office Action for related Korean Patent Application No. 2013-7027958 dated Jan. 10, 2014.
Office Action for related Singapore Patent Application No. 201201880-0 dated Nov. 12, 2013.
Univ Nanjing Polytechnic, "Preparation and use of heteropolyacid catalyst carried on dealuminized super-stable gamma zeolite," Espacenet, Publication date: Feb. 23, 2005; English Abstract of CN-1583253.
Shanxi Coal Chem Inst., "Catalyst for oxo-synthesis of dimethyl ether to produce methylal, prepn. method and application thereof," Espacenet, Publication Date: Jun. 28, 2006; English Abstract of CN-1792446.
English Translation of the First Office Action of related Chinese Patent Application No. 200980162504 dated Sep. 26, 2013.
Comments of the Examiner from First Office Action of related Chinese Patent Application No. 200980162504 dated Sep. 26, 2013.
Li, R. et al., "Research and Progress of Application of Heteropolyacid Catalysts," Journal of Mudanjiang Normal University, natural Science Edition, Dec. 31, 2007; Complete English Translation.
Chai, S. et al., "Sustainable production of acrolein: gas-phase dehydration of glycerol over 12-tungstophosphoric acid spported on $ZrO_2$ and $SiO_2$," Green Chem., 2008, vol. 10, pp. 1087-1093.
Chai, S. et al., "Sustainable production of acrolein: Preparation and characterization of zirconia-supported 12-tungstophosphoric acid catalyst for gas phase dehydration of glycerol," Applied Catalysis A: General, 2009, vol. 353, pp. 213-222.
Nippon Catalytic Chem Ind., "Process for dehydration of polyhydric alcohols," Espacenet, Publication Date: May 24, 2007; English Abstract of WO-2007-058221.
Tsukuda, E. et al., "Production of acrolein from glycerol over silica-supported heteropolyacids," Catalysis Communications, 2007, vol. 8, pp. 1349-1353.
Written Opinion of the International Searching Authority for PCT/JP2009/067115 dated Mar. 18, 2012.
Office Action for JP-2012-529412; dated Dec. 9, 2014; Nippon, Kayaku Kabushiki Kaisha.

* cited by examiner

CATALYST AND PROCESS FOR PREPARING ACROLEIN AND/OR ACRYLIC ACID BY DEHYDRATION REACTION OF GLYCERIN

This application is subject to a joint research agreement between Arkema France and Nippon Kayaku Co., Ltd.

TECHNICAL FIELD

This invention relates to a novel dehydration catalyst, in particular to a dehydration catalyst for producing acrolein or acrylic acid by catalytic dehydration of glycerin in gas phase or liquid phase, to a method for preparing the catalyst and to a process for producing acrolein and/or acrylic acid by using the catalyst.

BACKGROUND ART

Glycerin is obtained in large amount as a byproduct when bio-fuel is produced from bio resources that do not depend on fossil resources, and research of new uses of glycerin is under development.

We have proposed, in PCT/JP2009/057818 and PCT/JP2009/057819, an improved dehydration catalyst comprising mainly a compound in which protons in a heteropolyacid are exchanged at least partially with at least one cation selected from elements belonging to Group 1 to Group 16 of the Periodic Table of Elements.

WO2007/058221 discloses a process for producing acrolein by dehydration reaction of glycerin in gas-phase in the presence of heteropolyacid used as a solid acid catalyst. The heteropolyacid is those of Group 6 element such as tungstosilicic acid, tungstophosphoric acid and phosphomolybdic acid. These heteropolyacids are supported on bi-modal pore size distribution silica carrier and produce acrolein at a yield of 86%. This dehydration reaction of glycerin, however, is effected without oxidation gas but using nitrogen stream as carrier gas, so that deposition of carbon increase seriously and hence there is a problem of deterioration in time of stability, activity and selectivity of the catalysis.

Tsukuda et al. "Production of acrolein from glycerol over silica-supported heteropoly acid" CATALYSIS COMMUNICATIONS, vol. 8, no. 9, 21 Jul. 2007, pp 1349-1353, Chai et al., "Sustainable production of acrolein: gas phase dehydration of glycerol over 12-tungstophosphoric acid supported on $ZrO_2$ and $SiO_2$", GREEN CHEMISTRY, vol. 10, 2008, pp. 1087-1093, and Chai et al., "Sustainable production of acrolein: preparation and characterization of zirconia-supported 12-tungstophosphoric acid catalyst for gas phase dehydration of glycerol", APPLIED CATALYSIS A: GENERAL, vol. 353, 2009, pp. 213-222 disclose that silica or zirconia-supported heteropoly acid is effective as a catalyst for dehydration of glycerol.

However, there is no usable catalyst in the industrial scale at higher performance.

WO2007/058221 (Nippon Shokubai) discloses a process for dehydrating polyhydric alcohols by using a catalyst containing an element of group 6 (Cr, Mo, W), in particular, comprising a heteropolyacid which can be supported on a carrier containing Al, Si, Ti or Zr. Examples show the acrolein yield of 70% for $PW/Al_2O_3$ 70% for $PW/ZrO_2$, 87% for $SiW/SiO_2$ but the conversion decreases from 100% to 70% in 8 hours.

U.S. patent No. 2009054538 (BATTELLE) discloses catalyst composition comprising phosphotungstic or phosphomolybdic acid on silica support and the acrolein yields obtained are not over 71% with the catalysts.

U.S. Pat. No. 5,919,725 discloses a catalyst comprising heteropoly salts and heteropolyacid salts deposited on a porous support of silica, zirconia and titania. This catalyst is used for aromatic alkylation such as alkylation of phenol with olefins but there is no mention of glycerol dehydration.

U.S. Pat. No. 4,983,565 discloses a process for preparing a catalyst composition by impregnating titania pellets with an aqueous solution consisting of tungstosilicic acid or molybdosilicic acid or their salts followed by drying and calcination. The catalyst composition is prepared preferably by impregnating a preformed pellet by immersing titania pellets in an aqueous solution of the tungstosilicic acid or molybdosilicic acid, for example. However, this patent teaches nothing about such a feature defined in the present invention that protons in the heteropolyacid are exchanged by at least one cation selected from elements belonging to Group 1 to Group 16 of the Periodic Table of Elements. Still more, this catalyst is used to prepare linear polyethylenepolyamine but there is no mention in dehydration of glycerol.

DISCLOSURE OF INVENTION

Technical Problems

Therefore, an object of this invention is to provide a novel dehydration catalyst, in particular a dehydration catalyst for producing acrolein or acrylic acid by catalytic dehydration of glycerin in gas phase or liquid phase.

Another object of this invention is to provide a method for preparing the catalyst and to a process for producing acrolein and/or acrylic acid by using the catalyst.

Still another object of this invention is to provide a process for producing acrolein and acrylic acid from glycerin that is a material not derived from petroleum, at a high yield.

Technical Solution

A first subject of the present invention resides in a catalyst composition comprising at least an heteropolyacid that has been deposited on a porous titania carrier.

In a preferred embodiment, the catalyst composition of the present invention comprises at least an heteropolyacid in which protons in the heteropolyacid are exchanged at least partially by at least one cation selected from elements belonging to Group 1 to Group 16 of the Periodic Table of Elements that have been deposited on a porous titania carrier.

Another subject of the present invention resides in a method for preparing the catalyst composition comprising impregnating a titania carrier with a solution of heteropolyacid, drying and firing the resulting solid mixture, optionally secondly impregnating the resulting impregnated carrier with a solution of at least one metal selected from elements belonging to the Group 1 to Group 16 of the Periodic Table of Elements or onium, drying, and firing the resulting solid mixture.

The catalyst composition according to the present invention can be prepared also by the steps comprising impregnating a titania carrier with a solution of at least one metal selected from elements belonging to the Group 1 to Group 16 of the Periodic Table of Elements or onium, drying and firing the resulting solid mixture, secondly impregnating the resulting solid mixture with a solution of heteropolyacid, drying, and firing the resulting solid mixture. In a variation, more than two different elements can be impregnated successively in the first impregnation step by using a respective impregnation and calcination operation. The catalyst composition according to the present invention can be prepared also by the method comprising more than one cycle of impregnation and firing, in which each impregnation is effected with a solution of an element belonging to the Group 1 to Group 16 of the Periodic Table of Elements or onium or with a solution containing more than one element selected from the group comprising P, Si, W, Mo, Ti, Zr, V, Nb, Ta, Cr, Mn, Fe, Co, Ni, Cu, Zn, Ga, In, Tl, Sn, Pb, and in which at least one impregnation is made with an acid precursor.

Still other subject of the present invention resides in a process for preparing acrolein by dehydration of glycerin, carried out in the presence of the catalyst.

This invention has following features (1) to (21) taken separately or in combination:

(1) The porous titania carrier is covered at least partially by a compound represented by the formula (I):

$$H_a A_b [X_1 Y_c Z_d O_e] \cdot n H_2 O \quad (I)$$

in which
H is hydrogen,
A is more than one cation selected from elements belonging to Group 1 to Group 16 of the Periodic Table of Elements except hydrogen,
X is P or Si,
Y is more than one element selected from the group comprising W, Mo, Ti, Zr, V, Nb, Ta, Cr, Mn, Fe, Co, Ni, Cu, Zn, Ga, In, Tl, Sn and Pb,
Z is more than one element selected from the group comprising W, Mo, Ti, Zr, V, Nb, Ta, Cr, Mn, Fe, Co, Ni, Cu, Zn, Ga, In, Tl, Sn and Pb,
a, b, c, d and n satisfying following ranges:
$0 \leq a < 9$
$0 \leq b \leq 9$, preferably $0 < b \leq 9$
$0 < c \leq 12$
$0 \leq d < 12$ and $0 < c + d \leq 12$
$n \geq 0$
and e is a number determined by the oxidation of the elements.

(2) The titania carrier comprises rutile or anatase or amorphous titanium oxide.
(3) The titania carrier comprises at least 80% anatase.
(4) The titania carrier has a specific surface of 20 to 120 m²/g.
(5) The cation is at least one alkali metal cation.
(6) The alkali metal is cesium.
(7) The compound contains at least one element selected from the group comprising W, Mo and V.
(8) In the method for preparing the catalyst composition according to the present invention, one impregnation is made with a phosphotungstic acid or a phosphotungstate solution.
(9) In the method for preparing the catalyst composition according to the present invention, one impregnation is made with a silicotungstic acid or a silicotungstate solution.
(10) In the method for preparing the catalyst composition according to the present invention, one impregnation is made with a cesium salt solution.
(11) The impregnation is performed by a technique of pore volume impregnation or excess solution impregnation.
(12) The impregnation is performed in a fluidized bed or moving bed to obtain a composition usable in a fluidized bed type reactor.
(13) The firing (calcination) is carried out under an atmosphere of air, inert gas or a mixture of oxygen and inert gas, or under a reduced gas such as $H_2$.
(14) The firing (calcination) is effected at a temperature of 150 to 900° C. for 0.5 to 10 hours, preferably at a temperature of 350 to 650° C.
(15) The process for preparing acrolein by dehydration of glycerin is carried out in the presence of the catalyst according to the invention.
(16) The process for preparing acrolein or acrylic acid is effected in the presence of molecular oxygen, with the conditions disclosed for example in WO 06/087083 or WO 06/114506.
(17) The process for preparing acrolein or acrylic acid is effected in the presence of a gas containing propylene, as disclosed for example in WO 07/090990 and WO 07/090991, that is say to carry out the glycerol dehydration stage beneath the propylene oxidation reactor of the conventional process, taking benefit of the high temperature of the gas coming out of that stage containing mainly acrolein and some remaining propylene.
(18) The process for preparing acrolein carried out in a reactor of the plate heat exchanger type or in a fixed bed reactor or in a fluidized bed type reactor or in a circulating fluidized bed or in a moving bed.
(19) The resulting acrolein is further oxidized to produce acrylic acid.
(20) The process for preparing acrolein by dehydration of glycerin, carried out in the presence of the catalyst is followed by a second step of ammoxidation of acrolein to acrylonitrile, as described for example in WO 08/113927.
(21) The process for preparing acrolein by dehydration of glycerin, carried out in the presence of the catalyst has an intermediate step of partial condensation of water and heavy by-products issuing from the dehydration step, as described for example in WO 08/087315, dehydration of glycerin is carried out under a pressure of 0.1 MPa to 0.5 MPa for an intermediate step of partial condensation of water and heavy by-products issuing from the dehydration step.

Advantageous Effect

The catalyst according to this invention have following merits and advantages that are important in industrial uses:
(1) Acrolein and/or acrylic acid can be produced with higher yield.
(2) Deactivation of the catalyst is limited.
(3) The catalyst according to this invention can be regenerated at higher temperature comparing to the catalyst having no support (or carrier).
(4) The catalyst according to this invention maintains advantages of non-support catalyst. In fact, the resistance to water is remarkably improved. On the contrary, in case of the conventional heteropolyacid catalysts, deterioration or deactivation of catalysts is serious in the glycerin dehydration reaction in a gas phase reaction which is effected in the presence of excess amount of water, such a reaction using as a material an aqueous solution of glycerin at lower concentration, or in a liquid phase in which water or lower alcohol is used as a reaction medium. Still more, owing to the improvement in resistance to water, a problem of corrosion of reactors that was observed when acid catalyst was used can be also solved

BEST MODE FOR CARRYING OUT THE INVENTION

The heteropolyacid is known and has several structures such as Keggin type, Dawson type and Anderson type and possess generally such high molecular weight as 700 to 8,500. There are dimer complex forms and those dimer complex are included in the present invention.

The elements belonging to Group 1 to Group 16 of the Periodic Table of Elements may be sodium, potassium, rubidium, cesium, magnesium, calcium, strontium, barium, scandium, yttrium, lanthanoid, titanium, zirconium, hafnium, chromium, manganese, rhenium, iron, ruthenium, osmium, cobalt, rhodium, iridium, nickel, palladium, platinum, copper, silver, gold, zinc, gallium, indium, thallium, germanium, tin, lead, bismuth and tellurium. The onium salts of heteropolyacid may be amine salts, ammonium salts, phosphonium salts and sulfonium salts.

Ions of molybdenum and of tungsten form oxoacid in water and the oxoacids polymerize to form the polyoxoacid of high molecular weight. The polymerization may not be effected only with the same kind of oxoacids but also with other kinds of oxoacids. Heteropolyacid is a polyacid possessing polynuclear structure, obtained by condensation of more than two kinds of oxoacids. An atom which forms the center oxoacid is called as "hetero-atom", while atoms forming oxoacids surrounding the center oxoacid and obtained by the polymerization is called as "poly-atoms". The hetero-atom may be silicon, phosphorus, arsenic, sulfur, iron, cobalt, boron, aluminum, germanium, titanium, zirconium, cerium and chromium. Among them, phosphorus and silicon are preferable. The poly-atoms may be molybdenum, tungsten, vanadium, niobium and tantalum. Among them, molybdenum and tungsten are preferable. The heteropolyacids used in this invention to prepare a glycerin dehydration catalyst may be tungstophosphoric acid, tungstosilicic acid, phosphomolybdic acid and silico molybdic acid. The heteropolyacid may be a mixed coordinate comprising the hetero-atoms of phosphorus or silicon and the poly-atoms are mixed coordinate of molybdenum and tungsten, or mixed coordinate of tungsten and vanadium or mixed coordinate of vanadium and molybdenum.

In a preferred embodiment, the glycerin dehydration catalyst according to this invention comprises a compound in which at least part of protons in the heteropolyacid are exchanged with at least one cation of alkali metal.

The catalyst composition according to the present invention used for producing acrolein and acrylic acid from glycerin contains preferably at least one element selected from a group comprising W, Mo and V.

In a preferred embodiment, the alkali metal is preferably cesium and at least a part of protons in the heteropolyacid is exchanged with cesium. It is also possible to exchange at least a part of protons in the heteropolyacid with cesium and a part of remaining protons in the heteropolyacid is exchanged at least partially with at least one cation selected from elements belonging to Group 1 to Group 16 of the Periodic Table of Elements. Acrolein and acrylic acid can be produced at higher yield by using the glycerin dehydration catalyst composition according to the present invention. Resistance to water is increased by exchanging part of protons contained in the heteropolyacid with cesium, so that the life of catalyst is improved in comparison to heteropolyacid that is inherently water-soluble.

An amount of the aqueous solution of mineral salt of exchanging cation is determined in such a manner that an electric charge of cation to be added is equal to or less than an electric charge of the heteropolyanion. For example, when a cation with charges of r is added to a heteropolyanion with charges of $3^-$, the cation is added equal to or less than 3 equivalent to the heteropolyanion, and when a cation with charges of $3^+$ is added to a heteropolyanion with charges of $3^-$, the cation is added equal to or less than 1 equivalent to the heteropolyanion. When a plurality of cations are introduced, an amount of the cation is determined in such a manner that the total electric charge of the cations becomes equal to or less than an electric charge of the heteropolyanion. If an amount of an aqueous solution of inorganic salt or a proportion of the cation(s) to be exchanged with protons become excessive, the activity of catalyst is spoiled or the yields of acrolein and acrylic acid are lowered or the life of catalyst is shortened.

In a variation, the glycerin dehydration catalyst according to this invention contains further at least compound of elements belonging to Group 1 to Group 16 of the Periodic Table of Element in addition to the above compound. The compound of elements belonging to Group 1 to Group 16 of the Periodic Table of Element may be metal salts or onium salts. The metal salt may be salt of tellurium, platinum, palladium, iron, zirconium, copper, cerium, silver and aluminum. The onium salts may be amine salts, ammonium salts, phosphonium salts and sulfonium salts. The metal salt or the onium salt may be prepared from such materials as nitrates, carbonate, sulfates, acetates, hydroxides, oxides and halides of the metals or of onium but are not limited thereto. A proportion of the metal salt is 0.0001 to 60% by weight, preferably 0.001 to 30% by weight in term of the metal salts or the onium salt with respect to the above compound.

As the mostly preferred dehydration catalyst of glycerin, following composition that has been deposited on a porous titania represented by the general formula (I) is mentioned:

$$H_aA_b[X_1Y_cZ_dO_e].nH_2O \qquad (I)$$

in which

H is hydrogen,

A is at least one cation selected from elements belonging to Group 1 to Group 16 of the Periodic Table of Elements except H X is P or Si, Y is at least one element selected from the group comprising W, Mo, Ti, Zr, V, Nb, Ta, Cr, Mn, Fe, Co, Ni, Cu, Zn, Ga, In, Tl, Sn and Pb, Z is at least one element selected from the group comprising W, Mo, Ti, Zr, V, Nb, Ta, Cr, Mn, Fe, Co, Ni, Cu, Zn, Ga, In, Tl, Sn and Pb, and a, b, c and satisfying following ranges:

$0 \le a < 9$ $0 \le b \le 9$, preferably $0 < b \le 9$ $0 < c \le 12$ $0 \le d < 12$ and $0 < c + d \le 12$ e is a number determined by the oxidation of the elements and n is any positive number.

In the present invention, the above-mentioned compound is deposited on a titania carrier or support ("supported catalyst"). In this text, terms of carrier or support have the same meaning.

An amount of the above-mentioned compound represented by the formula (I) is 5 to 99.9% by weight, preferably 5 to 90% by weight to the weight of the carrier.

The catalyst may have any shape and can be granule, powder or monolith. In case of gas phase reactions, however, it is preferable to mold the catalyst into a shape of monolith, sphere, pellets, cylinder, hollow cylinder, bar or the like optionally with adding a molding aid or the catalyst is shaped into these configurations together with carrier and optional auxiliary agents. A size of molded catalyst is for example 1 to 10 mm for a fixed bed and less than 1 mm for a fluidized bed.

In case of a fluidized bed reactor for the process for preparing acrolein, it is preferred to have a powder with appropriate average particle size distribution namely between 40 and 300 μm, preferably between 60 and 150 μm.

The catalyst composition according to the present invention can be prepared by successive impregnation of a carrier with a solution of at least one metal selected from elements belonging to the Group 1 to Group 16 of the Periodic Table of Elements or onium and with a solution of heteropolyacid, and vice versa. The catalyst can also be prepared by successive impregnation of a carrier with a solution of heteropolyacid and with a solution of at least one metal selected from elements belonging to the Group 1 to Group 16 of the Periodic Table of Elements or onium. After each impregnation, the solid can be dried and fired as described below. Impregnation can be performed by the known techniques of pore volume impregnation or excess solution impregnation.

The catalyst composition can also be prepared by spay-drying method with a spray-dryer.

In this text, wordings of "firing" or "calcination" are used in the same meaning.

Namely, the catalyst composition according to the present invention can be prepared by impregnating a preformed pellet or porous titania carrier. For example, titania carrier is immersed in an aqueous solution of at least one metal selected from elements belonging to the Group 1 to Group 16 of the Periodic Table of Elements or onium. The resulting solid mixture is then dried and fired. In the present invention, the resulting solid mixture is secondly impregnating with a solution of heteropolyacid. Then, the resulting solid mixture is dried and fired to obtain an objective catalyst.

The solution of at least one metal selected from elements belonging to the Group 1 to Group 16 of the Periodic Table of Elements or onium can be an aqueous solution of halide, hydroxide, carbonate, acetate, nitrate, oxalate, phosphate or sulfate of metal or onium.

Alternately, the catalyst composition according to the present invention can be prepared by impregnating a titania carrier firstly with a solution of heteropolyacid. For example, an aqueous solution of heteropolyacid is prepared firstly. When the aqueous solution of heteropolyacid is prepared, it is preferable to remove waters contained in the heteropolyacid in a form of adsorptive water and crystal water partially or totally under vacuum or heat-drying. The resulting solid mixture is then dried and fired. In the second impregnation, the resulting impregnated carrier is impregnated with a solution of at least one metal selected from elements belonging to the Group 1 to Group 16 of the Periodic Table of Elements or onium, followed by drying and firing operations to obtain an objective catalyst.

Or, the catalyst composition according to the present invention can be prepared by the method comprising more than one cycle of impregnation and firing. In this case, each impregnation is effected with a solution of an element of the group 1 to belonging to the Group 1 to Group 16 of the Periodic Table of Elements or onium or with a solution containing more than one element selected from the group comprising P, Si, W, Mo, Ti, Zr, V, Nb, Ta, Cr, Mn, Fe, Co, Ni, Cu, Zn, Ga, In, Tl, Sn, Pb, and at least one impregnation is effected with an acid precursor. In a variation, the catalyst composition according to the present invention can be prepared by adding PW or Cs to titania powder firstly and then, without drying and firing operations, Cs or PW is added continuously.

Impregnation can be carried out at ambient temperature (about 20° C.). Higher temperatures of about 100° C. to about 150° C. may be used, if desired. This treatment may be continued, preferably with agitation, for about 0.1 to about 5 hours sufficient to permit the aqueous solution to penetrate the pores of the titania carrier. Suitably, the amount of aqueous solution of at least one metal selected from elements belonging to the Group 1 to Group 16 of the Periodic Table of Elements or onium and the heteropolyacid that is used should be adequate to permit full immersion of the titania carriers.

At the end of the immersion step, the excess aqueous solution can be evaporated from the treated titania carriers, or it can be removed from the aqueous solution and permitted to dry in a drying oven.

The exact nature of bonding of the catalyst composition according to the present invention is not completely understood.

The catalyst according to the present invention used in the glycerin dehydration may be anhydrides or hydrates. In fact, they can be used after pretreatment of firing and vacuum-drying or without pretreatment.

The calcination can be carried out in air or under inert gas such as nitrogen, helium and argon or under an atmosphere of mixed gas of air and inert gas usually or under reduction gas such as hydrogen or an atmosphere of mixed gas of hydrogen and inert gas in a furnace such as muffle furnace, rotary kiln, fluidized bed furnace. The furnace is not limited specially. The calcination can be effected even in a reaction tube which is used for the glycerin dehydration reaction. The firing temperature is usually 150 to 900° C., preferably 200 to 800° C. and more preferably 350 to 650° C. This can be determined by routine experimentation for a particular catalyst. Temperatures above 900° C. should be avoided. The calcination is continued usually for 0.5 to 10 hours.

The dehydration reaction of glycerin according to this invention can be carried out in gas phase or in liquid phase and the gas phase is preferable. The gas phase reaction can be carried out in a variety of reactors such as fixed bed, fluidized bed, circulating fluidized bed and moving bed. Among them, the fixed bed or the fluidized bed are preferable. Regeneration of the catalyst can be effected outside the reactor. When the catalyst is taken out of a reactor system for regeneration, the catalyst is burnt in air or in oxygen-containing gas. In case of liquid phase reaction, usual general reactors for liquid reactions for solid catalysts can be used. Since the difference in boiling point between glycerin (290° C.) and acrolein and acrylic acid is big, the reaction is effected preferably at relatively lower temperatures so as to distil out acrolein continuously.

The reaction temperature for producing acrolein and acrylic acid by dehydration of glycerin in gas phase is effected preferably at a temperature of 200° C. to 450° C. If the temperature is lower than 200° C., the life of catalyst will be shortened due to polymerization and carbonization of glycerin and of reaction products because the boiling point of glycerin is high. On the contrary, if the temperature exceeds 450° C., the selectivity of acrolein and acrylic acid will be lowered due to increment in parallel reactions and successive reactions. Therefore, more preferable reaction temperature is 250° C. to 350° C. The pressure is not limited specially but is preferably lower than 5 atm and more preferably lower than 3 atm. Under higher pressures, gasified glycerin will be re-liquefied and deposition of carbon will be promoted by higher pressure so that the life of catalyst will be shortened.

A feed rate of a material gas is preferably 500 to 10,000 h$^{-1}$ in term of the space velocity of GHSV. The selectivity will be lowered if the GHSV becomes lower than 500 h$^{-1}$ due to successive reactions. On the contrary, if the GHSV exceeds 10,000 h$^{-1}$, the conversion will be lowered.

The reaction temperature of the liquid phase reaction is preferably from 150° C. to 350° C. The selectivity will be spoiled under lower temperatures although the conversion is improved. The reaction pressure is not limited specially but the reaction can be carried if necessary under a pressurized conditions of 3 atm to 70 atm.

The material of glycerin is easily available in a form of aqueous solution of glycerin. Concentration of the aqueous solution of glycerin is from 5% to 90% by weight and more preferably 10% to 50% by weight. Too high concentration of glycerin will result in such problems as production of glycerin ethers or undesirable reaction between the resulting acrolein or acrylic acid and material glycerin. Temperature which is necessary to gasify glycerin is increased.

Now, the present invention will be explained in much detail with referring several examples, but this invention should not be limited to those described in following examples. In the following Examples and Comparative Examples, % means mole %.

EXAMPLES

Example 1

CsPW/TiO$_2$ 15 g of CsCO$_3$ were dissolved in deionised water to obtain an aqueous solution containing 7.6% of cesium carbonate. 10.2 g of this aqueous solution of cesium carbonate was sprayed onto 25 g of TiO$_2$ powder obtained by grinding anatase type TiO$_2$ pellets (ST31119 from Norpro Saint Gobain) to 35 to 48 mesh. The resulting powder was dried at 110° C. for 2 hours and then was fired in nitrogen atmosphere at 300° C. for 3 hours to obtain Cs/TiO$_2$.

7.0 g of tungstophosphoric acid was dissolved in 11.1 g of deionized water to obtain an aqueous solution of tungstophosphoric acid. 15 g of the resulting 38.8% aqueous solution of tungstophosphoric acid was then sprayed onto the above Cs/TiO$_2$. The resulting powder was then dried at 100° C. overnight and then was fired in nitrogen atmosphere at 400° C. for 3 hours to obtain a titania carrier supporting 20% of the cesium tungstophosphate. This titania carrier was sieved to obtain a particle size of 35 to 48 mesh.

The catalyst was evaluated in a fixed bed reactor operated under ambient pressure in a fixed bed. Namely, 7 cc of the resulting catalyst powder was packed in a quartz reaction tube (diameter of 16 mm).

An aqueous solution of glycerin (a concentration of 28% by weight) was fed to an evaporator at a flow rate of 26.9 g/hr together with nitrogen (4.9 NL/hr) and with oxygen (1.2 NL/hr) at 280° C. so that glycerin was gasified and the resulting gasified glycerin was passed through the fixed catalyst bed. The fixed catalyst bed was heated at a temperature of 275° C. Feed gas had a following composition in mol %:glycerin:oxygen:nitrogen:water=5.7:3.9:14.1:76.1. GHSV was 4,530 h$^{-1}$.

Products were condensed in a condenser and the collected product was quantitative-analyzed by gas chromatographs (HP 6890 Agilent, FFAP column, FID detector, CP4900 Varian, Silicaplot and Molecular Sieve 5 Å, TCD detectors). Proportions of products were corrected in factors from the results of the gas chromatograph to determine absolute amounts of products to calculate the conversion (%) of material (the conversion of glycerin), the selectivity of target substance (the selectivities of acrolein and of acrylic acid) and the yield of target substance (the yields of acrolein and of acrylic acid).

The conversion (%) of material, the selectivity of objective substance and the yield of objective substance are determined by following equations:

The conversion (%) of material=(a mole number of material reacted/a mole number of material supplied)×100

The selectivity (%) of objective substance=(a mole number of objective substance obtained/a mole number of material reacted)×100

The yield (%) of objective substance=(a mole number of objective substance obtained/a mole number of material fed)×100

Result is shown in Table 1.

TABLE 1

| | Time on stream (h) | |
|---|---|---|
| | 3 | 22 |
| Glycerin conversion (%) | 93 | 61 |
| Acrolein yield (%) | 76 | 53 |
| Acrolein selectivity (%) | 81 | 87 |
| Hydroxypropanone yield (%) | 1.1 | 2.0 |
| Acetaldehyde yield (%) | 0.9 | 0.8 |
| Propanaldehyde yield (%) | 0.9 | 0.5 |
| Acrylic acid yield (%) | 0.8 | 0.9 |
| CO yield (%) | 1.3 | 1.2 |
| CO$_2$ yield (%) | 0.9 | 1.0 |

Example 2

CsPW/TiO$_2$ 10 g of tungstophosphoric acid was dissolved in 150 ml of deionized water to obtain an aqueous solution of tungstophosphoric acid. 19.7 g of TiO$_2$ powder obtained by grinding anatase type TiO$_2$ pellets (ST31119 from Norpro Saint Gobain—BET surface 39 m$^2$/g) to 300 to 500 μm and drying at 110° C. overnight was added in obtained aqueous solution of tungstophosphoric acid, and then was mixed at room temperature for 2 hours. 2.26 g of 48.5% CsOH aqueous solution was diluted with 10 ml of deionized water. The resulting CsOH aqueous solution was dropped in above white slurry of tungstophosphoric acid and TiO$_2$, mixing this white slurry. The resulting slurry was evaporated at 60° C. by use of rotary-evaporator. The obtained powder was dried at 120° C. for 10 hours and then was calcined in air at 500° C. for 3 hours to obtain a titania carrier supporting 30% of Cs salt of tungstophosphoric acid. The obtained powder was pressed to pellets and then was sieved to obtain a particle size of 9 to 12 mesh, grinding above pellets of CsPW/TiO$_2$.

The catalyst was evaluated in a fixed bed reactor operated under ambient pressure in a fixed bed. Namely, 10 cc of the resulting catalyst granule was packed in a quartz reaction tube (diameter of 20 mm).

An aqueous solution of glycerin (a concentration of 30% by weight) was fed to an evaporator at a flow rate of 21 g/hr together with nitrogen (3.7 NL/hr) and with oxygen (1.0 NL/hr) at 300° C. so that glycerin was gasified and the resulting gasified glycerin was passed through the fixed catalyst bed. The fixed catalyst bed was heated at a temperature of 300° C. Feed gas had a following composition in mol %:glycerin:oxygen:nitrogen:water=6.3:4.0:14.9:74.8. GHSV was 2445 h$^{-1}$.

The collection, analytical method and calculation of products were the same way as Example 1.

TABLE 2

| | Time on stream (h) | |
|---|---|---|
| | 2 | 21 |
| Glycerin conversion (%) | 100 | 98 |
| Acrolein yield (%) | 78 | 78 |
| Acrolein selectivity (%) | 78 | 80 |
| Hydroxypropanone yield (%) | 0.0 | 0.4 |
| Acetaldehyde yield (%) | 2.1 | 3.5 |
| Propanaldehyde yield (%) | 0.1 | 0.4 |
| Acrylic acid yield (%) | 0.9 | 0.4 |
| CO yield (%) | 5.3 | 3.5 |
| $CO_2$ yield (%) | 3.1 | 2.1 |

Example 3

$HPW/TiO_2$ 2.7 g of tungstophosphoric acid (Aldrich) was dissolved in 8.5 g of deionized water to obtain an aqueous solution of tungstophosphoric acid. 7.6 g of the resulting aqueous solution was then sprayed onto 15.4 g of $TiO_2$ powder obtained by grinding anatase type $TiO_2$ pellets (ST31119 from Norpro Saint Gobain—BET surface 39 m²/g) to 35 to 48 mesh. The resulting powder was dried at 110° C. for 2 hours and then was fired in nitrogen atmosphere at 300° C. for 3 hours. The resulting powder was then dried at 100° C. overnight and then was fired in nitrogen atmosphere at 500° C. for 3 hours to obtain a titania carrier supporting 10% of tungstophosphoric acid. This titania carrier was sieved to obtain a particle size of 35 to 48 mesh, having a BET surface of 35 m²/g.

Procedure of catalyst test was reproduced as in example 1. Results are shown in table 3.

TABLE 3

| | Time on stream (h) | |
|---|---|---|
| | 3 | 24 |
| Glycerin conversion (%) | 100 | 81 |
| Acrolein yield (%) | 79 | 60 |
| Acrolein selectivity (%) | 79 | 74 |
| Hydroxypropanone yield (%) | 0.1 | 1.8 |
| Acetaldehyde yield (%) | 1.4 | 0.9 |
| Propanaldehyde yield (%) | 0.6 | 0.3 |
| Acrylic acid yield (%) | 0.3 | 0.9 |
| CO yield (%) | 1.3 | 1.1 |
| $CO_2$ yield (%) | 0.8 | 0.8 |

Example 4

$HSiW/TiO_2$ 3.0 g of tungstosilicic acid (Aldrich) was dissolved in 11.1 g of deionized water to obtain an aqueous solution of tungstosilicic acid. 11.8 g of the resulting aqueous solution was then sprayed onto 25 g of $TiO_2$ powder obtained by grinding anatase type $TiO_2$ pellets (ST31119 from Norpro Saint Gobain) to 35 to 48 mesh. The resulting powder was dried at 110° C. for 2 hours and then was fired in nitrogen atmosphere at 300° C. for 3 hours. The resulting powder was then dried at 100° C. overnight and then was fired in nitrogen atmosphere at 625° C. for 3 hours to obtain a titania carrier supporting 10% of silicotungstic acid. This titania carrier was sieved to obtain a particle size of 35 to 48 mesh.

Procedure of catalyst test was reproduced as in example 1. Results are shown in table 4.

TABLE 4

| | Time on stream (h) | |
|---|---|---|
| | 3 | 24 |
| Glycerin conversion (%) | 100 | 67 |
| Acrolein yield (%) | 79 | 55 |
| Acrolein selectivity (%) | 79 | 82 |
| Hydroxypropanone yield (%) | 1.5 | 2.4 |
| Acetaldehyde yield (%) | 0.9 | 0.8 |
| Propanaldehyde yield (%) | 1.1 | 0.8 |
| Acrylic acid yield (%) | 0.3 | 0.9 |
| CO yield (%) | 1.0 | 1.1 |
| $CO_2$ yield (%) | 0.7 | 0.8 |

These Examples reveal moreover that the supported catalyst according to the present invention shows such advantages that deactivation of the catalyst is limited and regeneration can be done at higher temperature comparing to the catalyst having no support, without spoiling great merits described in our previous applications of PCT/JP2009/057818 and PCT/JP2009/057819.

Example 5 and Comparative Examples 6 to 8

Tungstophosphoric acid on silicon oxide or alumina was prepared in the same manner as in example 3 with silicon oxide SS61138 (251 m²/g) and SS61137 (161 m²/g) from Norpro Saint Gobain and with aluminium oxide SA6578 from Norpro Saint Gobain.

Those catalysts were tested along with catalyst of example 3 in the conditions described in the table 5 below.

TABLE 5

| | Example | Comparative Example | | |
|---|---|---|---|---|
| | 5 | 6 | 7 | 8 |
| Acid | 10% tungstophosphoric | | | |
| Catalyst support | $TiO_2$ ST31119 | $SiO_2$ SS61138 | $SiO_2$ SS61137 | $Al_2O_3$ SA6578 |
| Reactant ratios glycerol/O2/N2/H2O | 2.8/1.7/14.3/81.2 | | | |
| GHSV (h-1) | 5100 h$^{-1}$ | | | |
| Oven temperature | 280° C. | | | |
| Time on stream (h) | 11 | 11 | 11 | 13 |
| Acrolein yield (%) | 75% | 10% | 18% | 18% |

The invention claimed is:

1. A process for preparing acrolein by dehydration of glycerin, carried out in the presence of a catalyst, wherein the catalyst composition comprises at least an heteropolyacid in which protons in the hetropolyacid may be partially exchanged by at least one cation of elements belonging to Group 1 to Group 16 of the Periodic Table of Elements that have been deposited on a porous titania carrier.

2. The process of claim 1, in which said porous titania carrier is covered at least partially by a compound represented by the formula (1):

in which
H is hydrogen,
A is more than one cation of an element belonging to Group 1 to Group 16 of the Periodic Table of Elements except hydrogen,
X is P or Si, Y is more than one of W, Mo, Ti, Zr, V, Nb, Ta, Cr, Mn, Fe, Co, Ni, Cu, Zn, Ga, In, Tl, Sn or Pb, Z is more than one of W, Mo, Ti, Zr, V, Nb, Ta, Cr, Mn, Fe, Co. Ni, Cu, Zn, Ga, In, Tl, Sn or Pb, a, b, c, d and n are:

$0 \leq a < 9$ $0 \leq b \leq 9$, $0 < c \leq 12$ and $0 \leq d < 12$ $n \geq 0$ and e is a number determined by the oxidation of the elements.

3. The process of claim 2, in which said compound contains at least one of W, Mo or V.

4. The process of claim 2, wherein $0 < b \leq 9$.

5. The process of claim 1, in which said titania carrier comprises rutile or anatase or amorphous titanium oxide.

6. The process of claim 1, in which said titania carrier comprises at least 80% anatase.

7. The process of claim 1, in which said cation is at least one alkali metal cation.

8. The process of claim 1, in which said alkali metal is cesium.

9. The process of claim 1, in which dehydration of glycerin is effected in the presence of molecular oxygen.

10. The process of claim 1 in which dehydration of glycerin is effected in the presence of a gas containing propylene.

11. The process of claim 1 carried out in a reactor of the plate heat exchanger type or in a fixed bed reactor or in a fluidized bed type reactor or in a circulating fluidized bed or in a moving bed.

12. The process of claim 1, in which the resulting acrolein is further oxidized to produce acrylic acid.

13. The process of claim 12, having an intermediate step of partial condensation of water and heavy by-products issuing from the dehydration step.

14. The process of claim 1, followed by second step of ammoxidation of acrolein to acrylonitrile.

15. A process for preparing acrolein by dehydration of glycerin, carried out in the presence of a catalyst, wherein the catalyst is prepared according to a method for preparing a catalyst composition comprising impregnating a titania carrier with a solution of at least one metal of Group 1 to Group 16 of the Periodic Table of Elements or onium, drying and firing the resulting solid mixture, secondly impregnating the resulting solid mixture with a solution of heteropolyacid, drying, and firing the resulting solid mixture.

16. The process of claim 15, in which one impregnation is made with a phosphotungstic acid or phosphotungstate solution.

17. The process of claim 15, in which one impregnation is made with a silicotungstic acid or silicotungstate solution.

18. The process of claim 15, in which one impregnation is made with a cesium salt solution.

19. A process for preparing acrolein by dehydration of glycerin, carried out in the presence of a catalyst, wherein the catalyst is prepared according to a method for preparing a catalyst composition comprising impregnating a titania carrier with a solution of heteropolyacid, drying and firing the resulting solid mixture, optionally secondly impregnating the resulting impregnated carrier with a solution of at least one metal of Group 1 to Group 16 of the Periodic Table of Elements or onium, drying, and firing the resulting solid mixture.

20. The process of claim 19, in which one impregnation is made with a phosphotungstic acid or phosphotungstate solution.

21. The process of claim 19, in which one impregnation is made with a silicotungstic acid or silicotungstate solution.

22. The process of claim 19, in which one impregnation is made with a cesium salt solution.

23. A process for preparing acrolein by dehydration of glycerin, carried out in the presence of a catalyst, wherein the catalyst is prepared according to a method for preparing a catalyst composition prepared by more than one cycle of impregnation and firing, in which each impregnation is effected with a solution of an element of Group 1 to Group 16 of the Periodic Table of Elements or onium or with a solution containing more than one of P, Si, W, Mo, Ti, Zr, V, Nb, Ta, Cr, Mn, Fe, Co, Ni, Cu, Zn, Ga, In, Tl, Sn, or Pb, and in which at least one impregnation is made with an acid precursor.

24. The process of claim 23, in which one impregnation is made with a phosphotungstic acid or phosphotungstate solution.

25. The process of claim 23, in which one impregnation is made with a silicotungstic acid or silicotungstate solution.

26. The process of claim 23, in which one impregnation is made with a cesium salt solution.

* * * * *